(12) United States Patent
Savage et al.

(10) Patent No.: US 11,911,269 B2
(45) Date of Patent: Feb. 27, 2024

(54) VALVE PROSTHESIS FRAMES

(71) Applicant: Medtronic CV Luxembourg S.A.R.L., Luxembourg (LU)

(72) Inventors: Padraig Savage, Ballybrit (IE); Joseph Callol, Santa Rosa, CA (US); Alaena DeStefano, Santa Ana, CA (US); Joshua Dwork, Santa Rosa, CA (US); Devin Gosal, Santa Rosa, CA (US); Karan Punga, Santa Rosa, CA (US); Finn Rinne, Santa Rosa, CA (US); Billy Tam, Santa Rosa, CA (US)

(73) Assignee: MEDTRONIC CV LUXEMBOURG S.A.R.L., Luxembourg (LU)

(*) Notice: Subject to any disclaimer, the term of this patent is extended or adjusted under 35 U.S.C. 154(b) by 37 days.

(21) Appl. No.: 17/688,147

(22) Filed: Mar. 7, 2022

(65) Prior Publication Data
US 2022/0183833 A1    Jun. 16, 2022

Related U.S. Application Data

(63) Continuation of application No. 16/816,454, filed on Mar. 12, 2020, now Pat. No. 11,298,226, which is a
(Continued)

(51) Int. Cl.
*A61F 2/24* (2006.01)
*A61F 2/915* (2013.01)

(52) U.S. Cl.
CPC .. *A61F 2/2418* (2013.01); *A61F 2002/91558* (2013.01); *A61F 2220/005* (2013.01);
(Continued)

(58) Field of Classification Search
CPC .................................................. A61F 2/2418
See application file for complete search history.

(56) References Cited

U.S. PATENT DOCUMENTS

| 6,190,406 B1 | 2/2001 | Duerig et al. | |
| 6,312,456 B1 * | 11/2001 | Kranz | A61F 2/91 |
| | | | 623/1.13 |

(Continued)

FOREIGN PATENT DOCUMENTS

| WO | 9965418 A1 | 12/1999 |
| WO | 2011/137531 A1 | 11/2011 |

(Continued)

OTHER PUBLICATIONS

Communication pursuant to Article 94(3) EPC dated Nov. 12, 2018 in European Patent Application No. 14 703460.7.
(Continued)

*Primary Examiner* — Suba Ganesan
(74) *Attorney, Agent, or Firm* — MEDLER FERRO WOODHOUSE & MILLS PLLC

(57) ABSTRACT

A prosthesis can include a collapsible, reexpandable frame comprising first, second, and third sets of struts that define first and second rows of expandable cells. In some embodiments, the struts of the first, second, and third set of struts can be tapered. In some embodiments, the frame can include an intermediate section and an inflow section that is proximal to the intermediate section. The inflow section can include a concave saddle portion that is adjacent the intermediate section, and an outwardly flared portion.

17 Claims, 9 Drawing Sheets

Related U.S. Application Data continuation of application No. 13/740,861, filed on Jan. 14, 2013, now Pat. No. 10,617,517.

(52) U.S. Cl.
CPC ... *A61F 2230/005* (2013.01); *A61F 2230/008* (2013.01); *A61F 2230/0013* (2013.01); *A61F 2230/0054* (2013.01); *A61F 2230/0078* (2013.01); *A61F 2250/0037* (2013.01)

(56) References Cited

U.S. PATENT DOCUMENTS

| | | | |
|---|---|---|---|
| 6,706,062 | B2 | 3/2004 | Vardi et al. |
| 7,670,367 | B1 | 3/2010 | Chouinard et al. |
| 7,678,142 | B2 | 3/2010 | Vardi et al. |
| 7,914,569 | B2 | 3/2011 | Nguyen et al. |
| 7,993,388 | B2 | 8/2011 | Lee et al. |
| D652,927 | S | 1/2012 | Braido et al. |
| D653,342 | S | 1/2012 | Braido et al. |
| 8,105,373 | B2 | 1/2012 | Girton et al. |
| 2001/0029397 | A1 | 10/2001 | Thompson |
| 2003/0074051 | A1 | 4/2003 | Freislinger Luehrs |
| 2004/0243216 | A1 | 12/2004 | Gregorich |
| 2006/0235506 | A1 | 10/2006 | Ta et al. |
| 2006/0259136 | A1 | 11/2006 | Nguyen et al. |
| 2008/0097579 | A1 | 4/2008 | Shanley et al. |
| 2008/0221661 | A1 | 9/2008 | Bidne et al. |
| 2010/0049313 | A1* | 2/2010 | Alon ............... A61F 2/2439 623/2.11 |
| 2010/0168839 | A1 | 7/2010 | Braido et al. |
| 2010/0174358 | A1 | 7/2010 | Rabkin et al. |
| 2010/0191320 | A1 | 7/2010 | Straubinger et al. |
| 2011/0264196 | A1 | 10/2011 | Savage et al. |
| 2011/0319989 | A1* | 12/2011 | Lane ............... A61F 2/2412 623/2.37 |
| 2012/0053681 | A1 | 3/2012 | Alkhatib et al. |
| 2012/0197390 | A1 | 8/2012 | Alkhatib et al. |
| 2012/0226346 | A1 | 9/2012 | Boismier et al. |
| 2012/0277848 | A1 | 11/2012 | Roeder et al. |
| 2014/0018915 | A1* | 1/2014 | Biadillah ............ A61F 2/2418 623/2.17 |
| 2014/0123529 | A1* | 5/2014 | Williams ............ B08B 9/0436 42/95 |

FOREIGN PATENT DOCUMENTS

| | | |
|---|---|---|
| WO | 2012/048035 A2 | 4/2012 |
| WO | 2013/086413 A1 | 6/2013 |

OTHER PUBLICATIONS

PCT Search Report and Written Opinion for PCT/US2014/010791, dated May 9, 2014.

\* cited by examiner

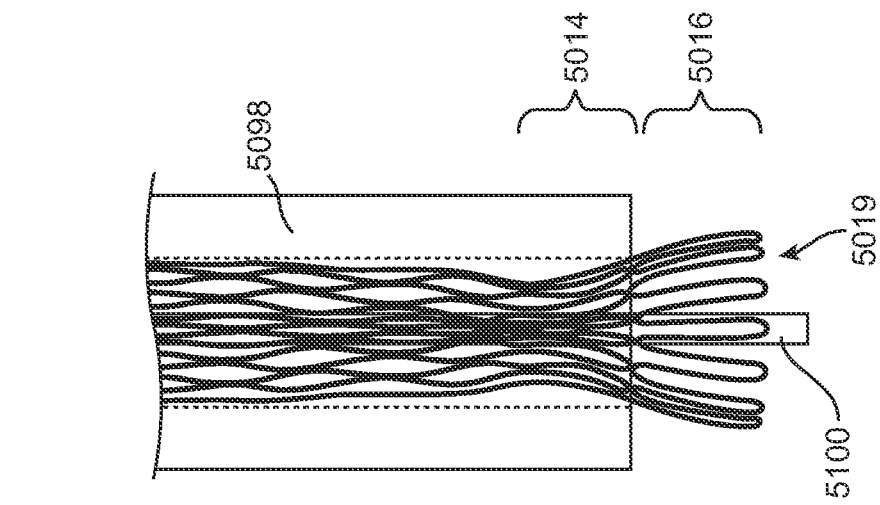
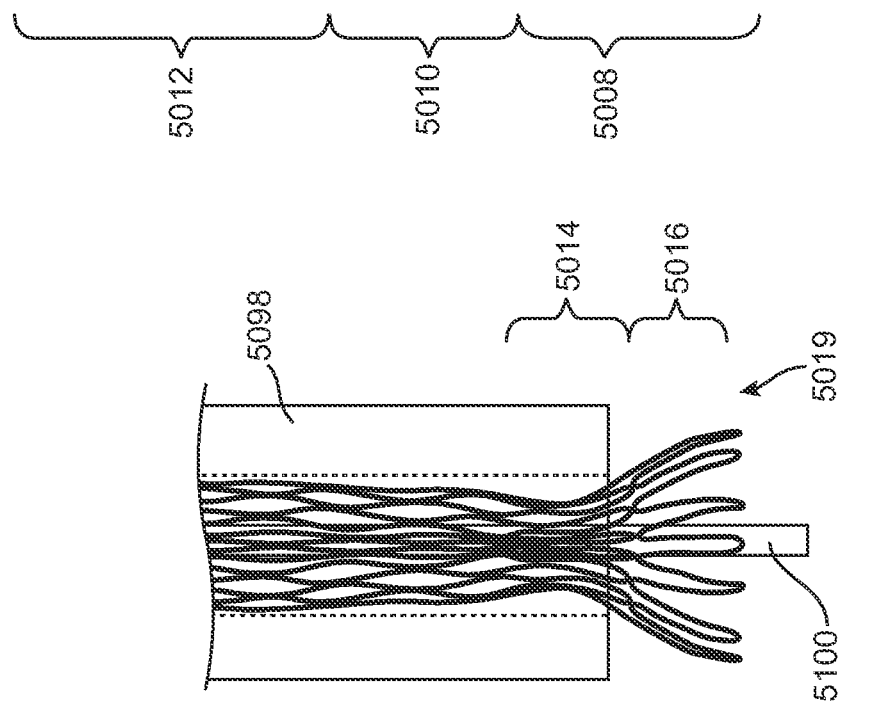

VALVE PROSTHESIS FRAMES

CROSS-REFERENCE TO RELATED APPLICATION

This application is a continuation of U.S. patent application Ser. No. 16/816,454 filed Mar. 12, 2020, which is a continuation of U.S. patent application Ser. No. 13/740,861, filed Jan. 14, 2013, now U.S. Pat. No. 10,617,517, each of which is hereby incorporated by reference in its entirety for all purposes.

BACKGROUND

Field

Embodiments of the present invention relate to frames and, particularly, to frames for valve prostheses.

Background

Patients suffering from valve regurgitation or stenotic calcification of the leaflets can be treated with a heart valve replacement procedure. A traditional surgical valve replacement procedure requires a sternotomy and a cardiopulmonary bypass, which creates significant patient trauma and discomfort. Traditional surgical valve procedures can also require extensive recuperation times and may result in life-threatening complications.

One alternative to a traditional surgical valve replacement procedure is delivering the replacement heart valve prosthesis using minimally-invasive techniques. For example, a heart valve prosthesis can be percutaneously and transluminally delivered to an implantation location. In such methods, a heart valve prosthesis can be compressed to be loaded on a delivery catheter; advanced to the implantation location; and re-expanded to be deployed at the implantation location. For example, a catheter loaded with a compressed heart valve prosthesis can be introduced through an opening in the femoral artery and advanced through the aorta to the heart. At the heart, the prosthesis can be re-expanded to be deployed at the aortic valve annulus, for example.

While the valve prosthesis is being compressed, for example, during loading or recapture within a delivery sheath of the delivery system, the prosthesis frame can infold. That is, the frame can buckle or fold over on itself. Infolding creates a risk that the frame may remain folded over when the valve prosthesis is deployed, which may cause valve assembly damage, device migration, paravalvular leakage, or other performance problems. Accordingly, there is a need for a valve prosthesis that reduces the risk of infolding.

BRIEF SUMMARY

In some embodiments, a prosthesis can include a collapsible and re-expandable frame. The frame can have an inflow edge and a longitudinal axis. The frame can be made of first, second, and third sets of struts. The struts of the first set of struts are connected to adjacent struts of the first set of struts at a first plurality of nodes at the inflow edge. The respective struts of the first and second sets of struts are connected at a second plurality of nodes to define a first row of expandable cells. Respective struts of the second and third sets of struts are connected at a third plurality of nodes to define a second row of expandable cells. The first row of expandable cells is proximal to the second row of expandable cells. Each node of the second plurality of nodes has a first length, and each node of the third plurality of nodes has a second length. The first length can be longer than the second length.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form part of the specification, illustrate embodiments of the present invention and, together with the description, further serve to explain the principles of the invention and to enable a person skilled in the relevant art(s) to make and use the invention.

FIGS. 5A-5G illustrate a valve prosthesis being retracted within a delivery sheath according to an embodiment.

Figure 1:
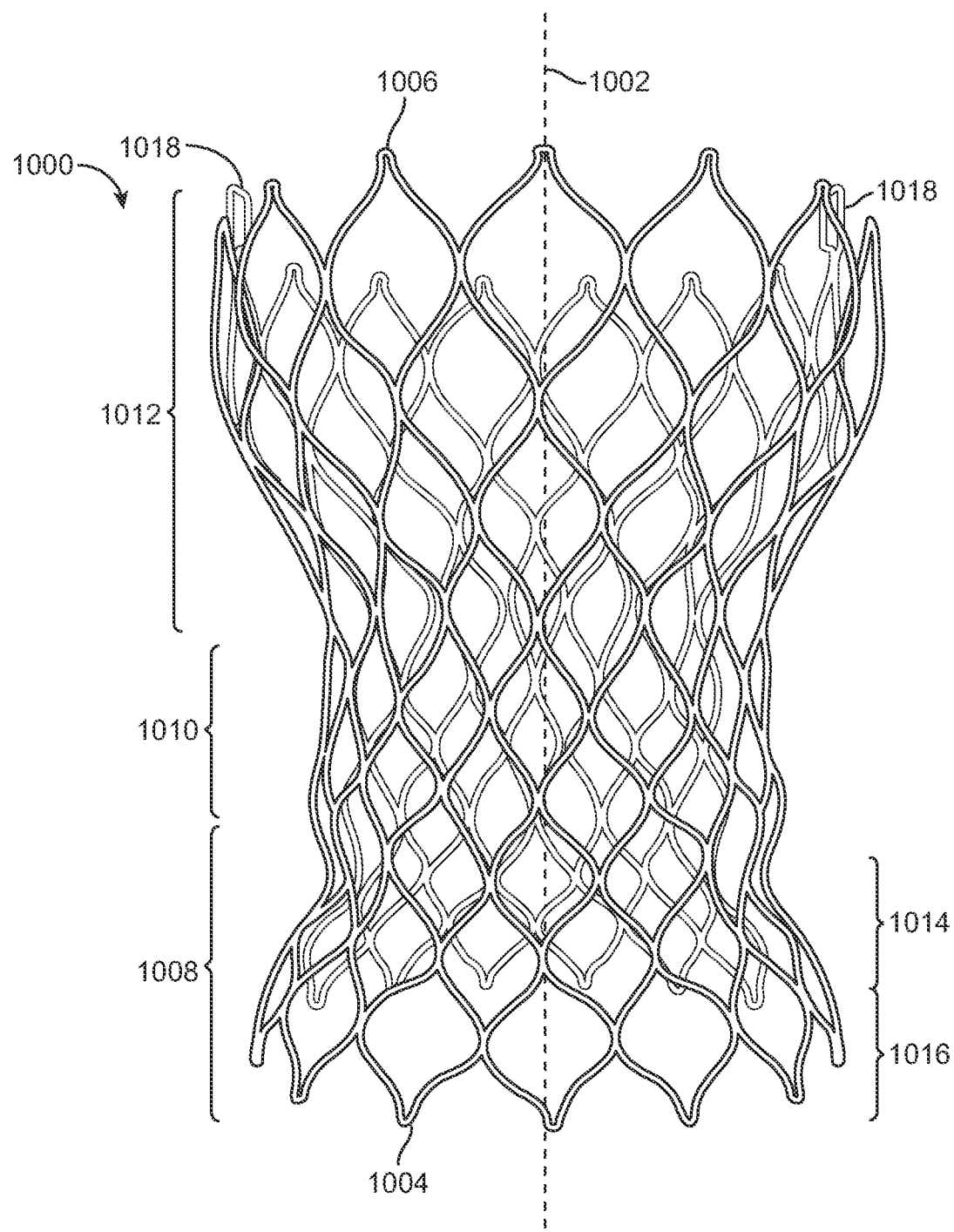
FIG. 1 illustrates a valve prosthesis frame according to an embodiment.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses embodiments that incorporate the features of this invention. The disclosed embodiments merely exemplify the invention. The scope of the invention is not limited to the disclosed embodiments. The invention is defined by the claims appended hereto.

The embodiments described, and references in the specification to "one embodiment," "an embodiment," "an example embodiment," "some embodiments," "example," etc., indicate that the embodiments described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

In this application, the term "proximal" means situated nearer to the upstream or inflow side of the valve prosthesis, and the term "distal" means situated nearer to the downstream or outflow side of the valve prosthesis.

A valve prosthesis according to various embodiments can be used to replace the function of a native cardiac valve, for example, the tricuspid valve, the pulmonary valve, the mitral valve, and the aortic valve. In some embodiments, the heart valve prosthesis can be configured to be collapsed to a small diameter condition such that the valve prosthesis can be delivered into a patient's body using minimally invasive techniques. For example, the valve prosthesis can be delivered using a catheter, a laparoscopic instrument, or any other suitable delivery device. In some embodiments, the valve prosthesis can be delivered to the heart using a transfemoral, transapical, transaxial, transaortic, or transseptal approach.

In some embodiments, the valve prosthesis can be configured to be re-expandable such that once the collapsed heart valve prosthesis is delivered to a desired implantation site the valve prosthesis can be deployed by re-expanding the valve prosthesis to a larger diameter condition to securely engage the surrounding anatomy. For example, an aortic valve prosthesis may be expanded to engage the aorta, the aortic annulus, the left ventricle outflow tract, or combinations thereof. After deployment, the valve prosthesis can function as a one-way valve, permitting blood flow in one direction (a downstream or distal direction) and preventing blood flow in an opposite direction (an upstream or proximal direction).

In some embodiments, the valve prosthesis includes a frame and a valve assembly coupled thereto. The frame supports the valve assembly. In some embodiments, the frame can be configured to be self-expandable or balloon expandable. The frame can be made from any suitable biocompatible metal and synthetic material. For example, suitable biocompatible metals can include nickel, titanium, stainless steel, cobalt, chromium, alloys thereof (e.g., nitinol), or any other suitable metal. And for example, suitable biocompatible synthetic materials can include thermoplastics or any other suitable synthetic material.

In some embodiments, the valve assembly includes a plurality of leaflets. In some embodiments, the valve assembly can also include a skirt. The valve assembly can be made from any suitable synthetic or biological material. For example, suitable biological materials can include mammalian tissue such as porcine, equine, or bovine pericardium.

FIG. 1 illustrates a frame 1000 of a valve prosthesis according to an embodiment. Frame 1000 has an longitudinal axis 1002. Frame 1000 also includes an inflow edge 1004 and an outflow edge 1006.

Frame 1000 can have an inflow section 1008, an intermediate section 1010, and an outflow section 1012. In some embodiments, inflow section 1008 can include a saddle portion 1014 and an outwardly flared portion 1016. Saddle portion 1014 can be concave—curving or bending inward towards longitudinal axis 1002 as shown in FIG. 1. In some embodiments, the contour of saddle portion 1014 forms a smooth curve. Outwardly flared portion 1016 can include at least one portion that extends outward from longitudinal axis 1002 in a proximal direction. In some embodiments, outwardly flared portion 1016 is convex—curving or bending outward away from longitudinal axis 1002 as shown in FIG. 1. In some embodiments, the contour of outwardly flared portion 1016 forms a smooth convex curve. As shown in FIG. 1, the transition between saddle portion 1014 and outwardly flared portion 1016 can form a smooth curve. In some embodiments, portion 1016 also includes an inwardly flared portion that defines inflow edge 1004, which can reduce the risk of heart block.

In some embodiments, inflow section 1008 may have other configurations. For example, inflow section 1008 may not have saddle portion 1014 or outwardly flared portion 1016.

Intermediate section 1010 is adjacent inflow section 1008. In some embodiments, intermediate section 1010 can be adjacent saddle portion 1014 of inflow section 1008. In some embodiments, the contour of intermediate section 1010 is generally parallel to longitudinal axis 1002. For example, the contour of intermediate section 1010 can taper slightly inward (as shown in FIG. 1) or outward as it extends in the distal direction, or can be exactly parallel to longitudinal axis 1002. In some embodiments, intermediate section 1010 can have other suitable configurations.

Figure 3:
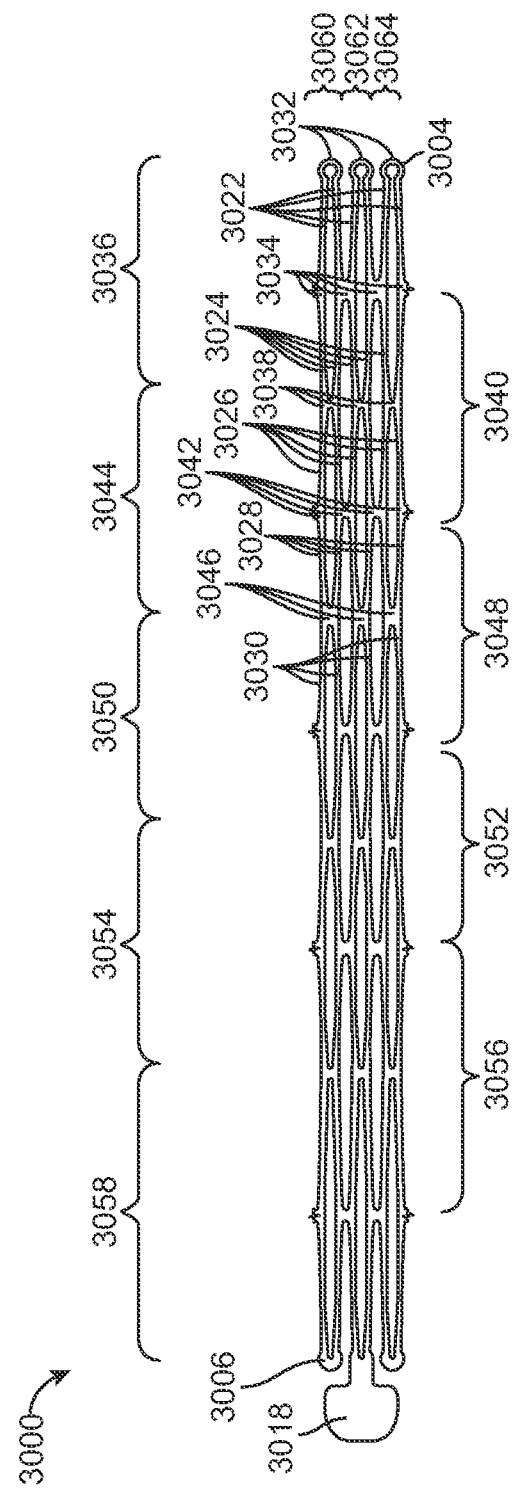
FIG. 3 illustrates a partial view of a valve prosthesis frame in an original, manufactured condition according to an embodiment.

Outflow section 1012 is adjacent intermediate section 1010. In some embodiments, outflow section 1012 includes one or more coupling elements 1018. For example, frame 1000 can have one, two, three, or more than three coupling elements 1018. Coupling elements 1018 are configured to selectively engage a delivery catheter system to coupling frame 1000 to the delivery catheter system. For example, as shown in FIG. 1, coupling elements 1018 can be rectangular tabs having a center opening that extend from outflow edge 1006. In some embodiments, coupling elements 1018 can have other shape configurations, for example, a solid paddle configuration as shown in FIG. 3. In some embodiments, outflow section 1012 includes an outwardly flared portion that is adjacent intermediate portion 1010. The contour surface of the outwardly flared portion extends away from longitudinal axis 1002 in the distal direction. In some embodiments, outflow section 1012 also includes a second portion that extends generally parallel to longitudinal axis 1002 or, in some embodiments, towards longitudinal axis 1002 to reduce the risk of tissue damage after being implanted. This second portion can define outflow edge 1006.

In some embodiments, frame 1000 is configured to be implanted at the aortic valve. Accordingly, inflow section 1008 can be configured to have an expanded diameter such that inflow section 1008 engages the outflow tract of the left ventricle. Saddle portion 1014 can be configured to have an expanded diameter such that saddle portion 1014 engages the transition between the native aortic annulus and the left ventricle outflow tract. In some embodiments, inflow section 1008 can be configured such that outwardly flared portion 1016 can contact the native aortic annulus. Intermediate section 1010 can be configured to have an expanded diameter such that intermediate section 1010 engages the native aortic annulus or leaflets. Outflow section 1012 can be configured to have an expanded diameter such that outflow section 1012 engages the aorta at a supra-coronary position. In some embodiments, the outwardly flared configuration of the first portion of outflow section 1012 is configured to provide a radial gap between frame 1000 and the aorta. This radial gap can reduce the risk that the coronary arteries will be blocked.

In some embodiments, frame 1000 is configured to be implanted at other locations, for example, at the mitral valve or completely within the aorta.

Figure 2:
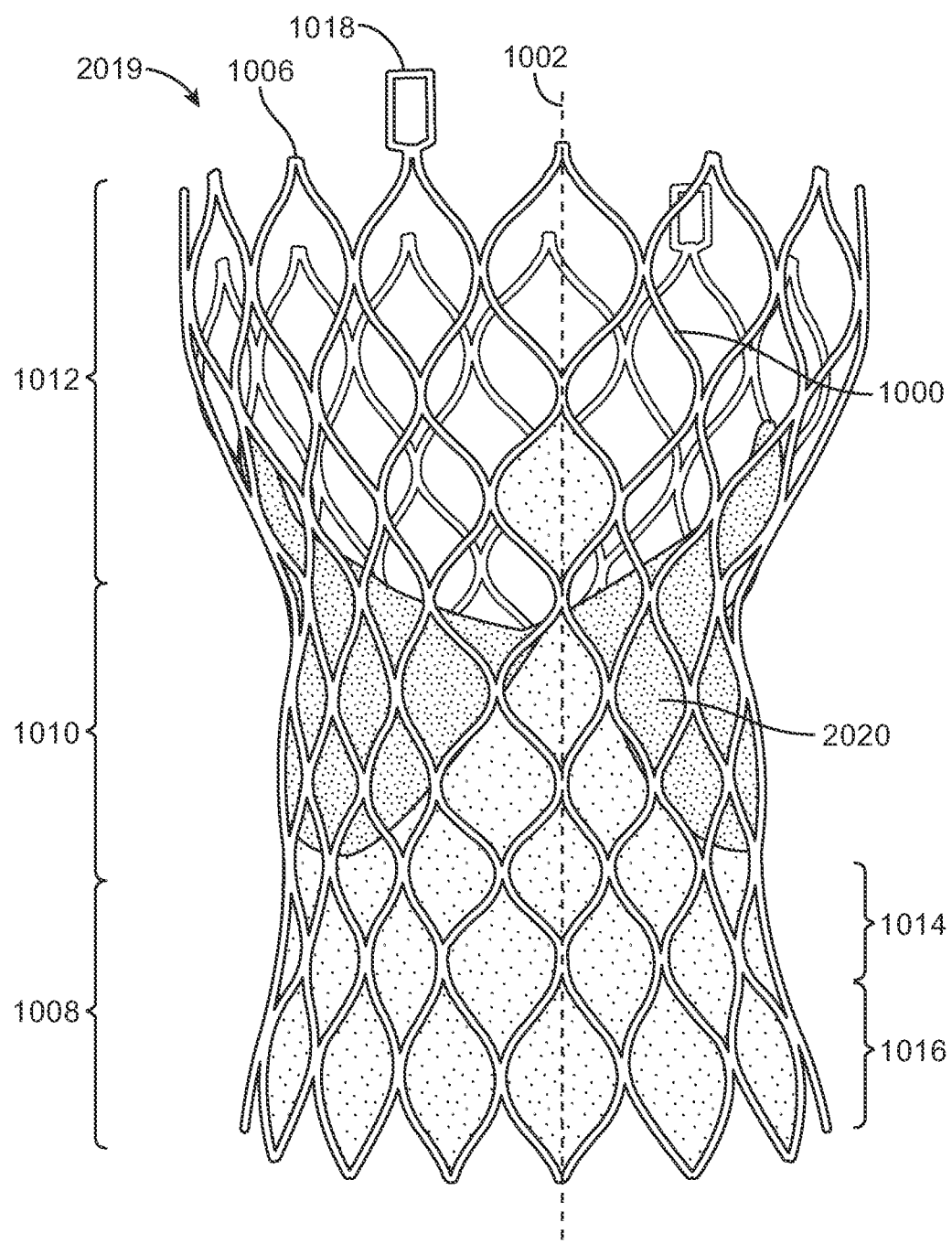
FIG. 2 illustrates a valve prosthesis including the frame illustrated in FIG. 1 and a valve assembly coupled to the frame according to an embodiment.

FIG. 2 illustrates a valve prosthesis 2019 that includes frame 1000 and a valve assembly 2020 according to an embodiment. In some embodiments, valve assembly 2020 includes a plurality of leaflets, for example, three leaflets.

Valve assembly 2020 can be coupled to frame 1000 using any suitable attachment mechanism, for example, sutures or adhesive.

In some embodiments, as shown in FIGS. 1 and 2, frame 1000 can include a plurality of struts forming a plurality of expandable cells. In some embodiments, this strut pattern is formed by known techniques of removing material from a substrate. For example, frame 1000 can be formed by laser cutting the pattern in a single tube or sheet of material, or by chemical etching. In some embodiments, the strut pattern is formed by welding or otherwise securing struts in the desired pattern.

FIG. 3 illustrates a portion of a frame 3000 of a valve prosthesis in its original manufactured condition—prior to being compressed or expanded—according to an embodiment. The pattern shown in FIG. 3 can be repeated around the entire circumference of frame 3000. In some embodiments, frame 1000 of FIGS. 1 and 2 can have an original manufactured condition as shown in FIG. 3.

In some embodiments, frame 3000 can include a plurality of sets of struts joined at respective nodes to define a plurality of rows of expandable cells. For example, as shown in FIG. 3, frame 3000 includes at least a first set of struts 3022, a second set of struts 3024, a third set of struts 3026, a fourth set of struts 3028, and a fifth set of struts 3030. In some embodiments, each set of struts 3022, 3024, 3026, 3028, and 3030 can have an undulating pattern, for example, a sinusoidal pattern or a zigzag pattern.

Each proximal end of the struts of first set 3022 are coupled to a proximal end of an adjacent strut of first set 3022 at a first plurality of nodes 3032. First plurality of nodes 3032 can define an inflow edge 3004 of frame 3000. The struts of first set 3022 can be coupled to respective struts of second set 3024 at a second plurality of nodes 3034 to form a first row of expandable cells 3036. The struts of second set 3024 can be coupled to respective struts of third set 3026 at a third plurality of nodes 3038 to form a second row of expandable cells 3040. The struts of third set 3026 can be coupled to respective struts of fourth set 3028 at a fourth plurality of nodes 3042 to form a third row of expandable cells 3044. The struts of fourth set 3028 can be coupled to respective struts of fifth set 3030 at a fifth plurality of nodes 3046 to form a fourth row of expandable cells 3048. This strut pattern can be axially repeated to form a plurality of rows of expandable cells along an entire longitudinal length of valve prosthesis frame 3000. For example, the strut pattern can be axially repeated to form fifth, sixth, seventh, eighth, and ninth rows of expandable cells 3050, 3052, 3054, 3056, and 3058 as shown in FIG. 3.

In some embodiments, the struts or nodes substantially and circumferentially aligned with a coupling element 3018 of frame 3000 can be configured to be less stiff than struts or nodes that are not axially aligned with a coupling element 3018. For example, as shown in FIG. 3, the struts and nodes forming a column of expandable cells 3062, which is axially aligned with coupling element 3018, can be configured to be less stiff than the struts and nodes forming columns of expandable cells 3060 and 3064, which is not axially aligned with coupling element 3018. In some embodiments such stiffness variations can be achieved by varying the shape of the struts axially aligned with coupling element 3018. For example, the widths and/or or thicknesses of the struts axially aligned with coupling element 3018 can be smaller than the widths and/or thicknesses of the struts that are not axially aligned with coupling element 3018. In some embodiments such stiffness variations can be achieved by varying the shape of the nodes axially aligned with coupling element 3018. For example, the lengths, widths, and/or thicknesses of the nodes connecting the struts axially aligned with coupling element 3018 can be smaller than the lengths, widths, and/or thicknesses of the nodes connecting the struts that are not axially aligned with coupling element 3018. In some embodiments in which the struts that are axially aligned with coupling element 3018 are configured to be less stiff than the struts that are not axially aligned with coupling element 3018, the risk of infolding is reduced.

In some embodiments, the struts or nodes substantially and circumferentially aligned with a coupling element 3018 of frame 3000 can be configured to be stiffer than or about equally stiff as struts or nodes that are not circumferentially axially aligned with a coupling element 3018.

Figure 4:
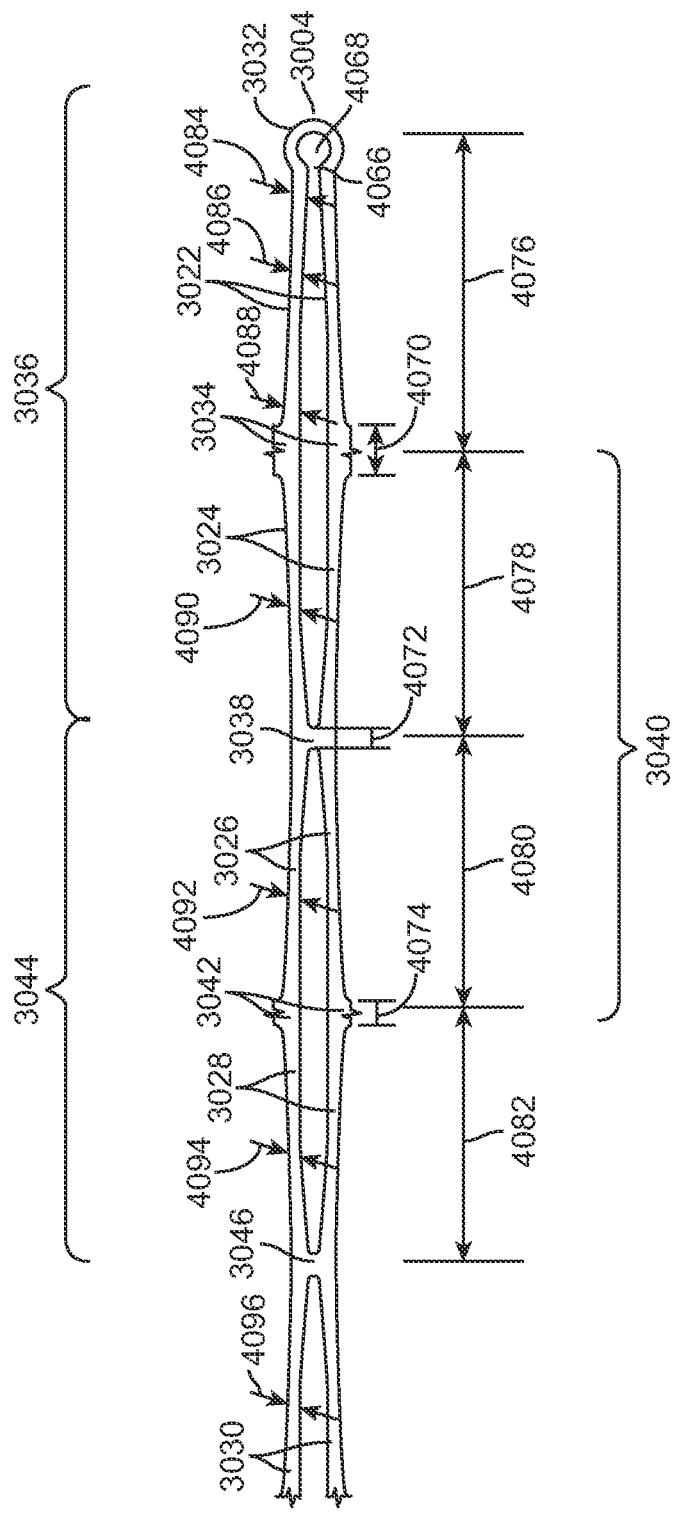
FIG. 4 illustrates an enlarged view of selected portion of the frame depicted in FIG. 3.
Figure 5A:
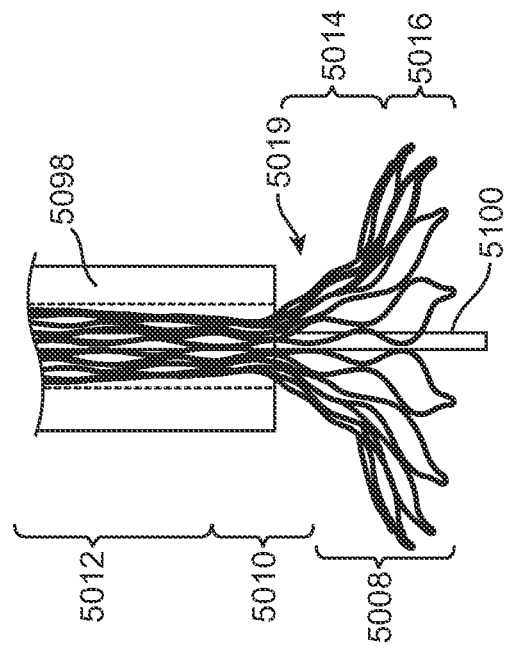
Figure 5B:
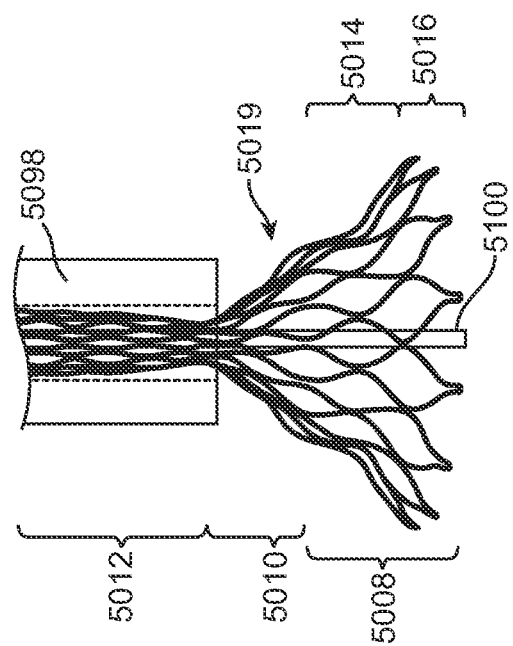
Figure 5C:
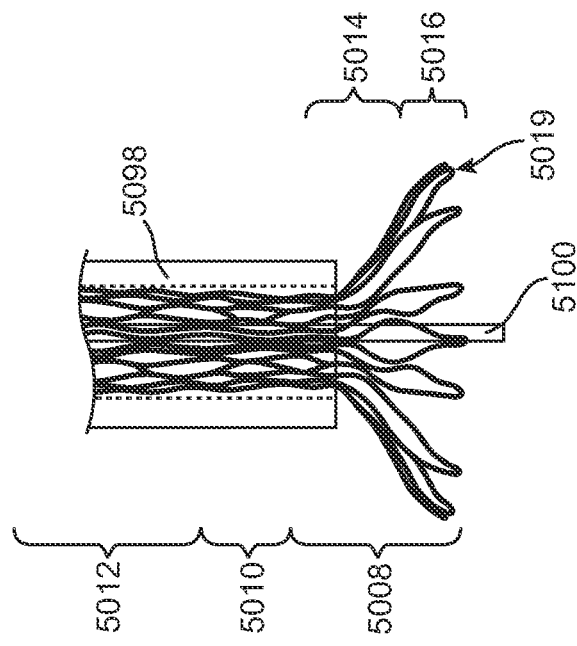
Figure 5D:
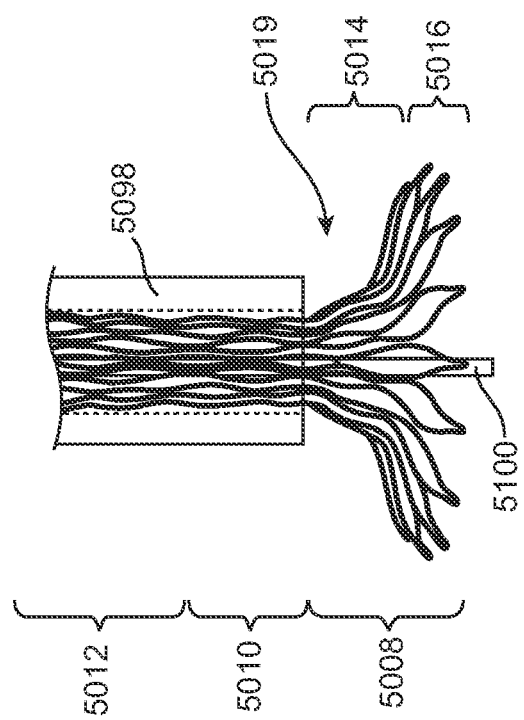
Figure 5G:
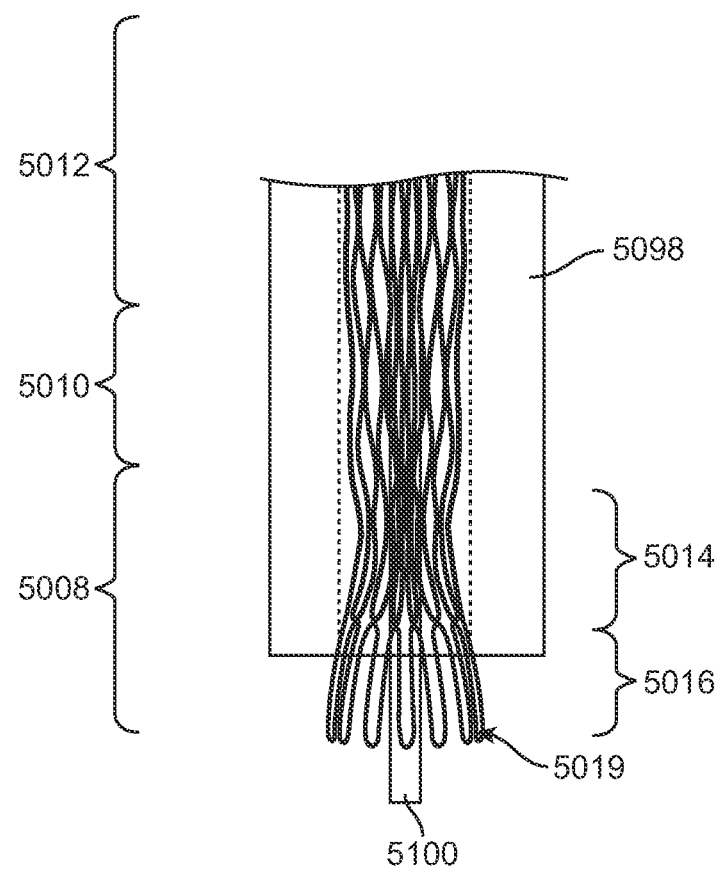

FIG. 4 illustrates an enlarged view of a selected portion of frame 3000 depicted in FIG. 3, for example, a portion of column 3060. In some embodiments, first plurality of nodes 3032 can define a keyhole-shaped opening. For example, the openings defined by first plurality of nodes 3032 can each comprise a distal portion 4066 and a proximal portion 4068. The width of the opening at distal portion 4066 is smaller than the width of the opening at proximal portion 4068. In some embodiments in which first plurality of nodes 3032 define keyhole-shaped openings, the forces generated by compressing frame 3000 can be better distributed away from the apices of first plurality of nodes 3032 at inflow edge 3004. Such a force distribution can allow frame 3000 to be more evenly compressed while still maintaining strength, which reduces the risk of infolding.

In some embodiments, a length 4070 of second plurality of nodes 3034 is greater than a length 4072 of third plurality of nodes 3038. In some embodiments, length 4070 is greater than a length 4074 of fourth plurality of nodes 3042. In some embodiments, length 4070 and length 4074 are in a range from about 0.1 mm to about 10 mm. For example, length 4070 can range from about 0.1 mm to about 1.5 mm, and lengths 4072 and 4074 can range from about 0.1 mm to about 1.2 mm. In some embodiments, lengths 4070, 4072, and 4074 are less than about 0.1 mm or more than about 1.5 mm, for example, about 10 mm. In some embodiments in which length 4070 is greater than length 4072 and/or length 4074, the forces generated while compressing frame 3000 can be more evenly distributed towards the struts of first set 3022. Such a force distribution can help minimize force localizations, which reduces the risk of infolding.

In some embodiments, a length 4076 between a center of first plurality of nodes 3032 and a center of second plurality of nodes 3034 is greater than a length 4078 between a center of second plurality of nodes 3034 and a center of third plurality of nodes 3038. In some embodiments, length 4076 is greater than a length 4080 between a center of third plurality of nodes 3038 and a center of fourth plurality of nodes 3042. In some embodiments, length 4076 is greater than a length 4082 between a center of fourth plurality of nodes 3042 and a center of fifth plurality of nodes 3046. In some embodiments, lengths 4076, 4078, 4080, and 4082 can be in a range from about 1 mm to about 50 mm. For example, length 4076 can range from about 3 mm to about 7 mm, and lengths 4078, 4080, and 4082 can range from about 2.5 mm to about 6.5 mm. In some embodiments in which length 4076 is greater than lengths, 4078, 4080, and 4082, the forces generated by compressing frame 3000 can be better distributed along the lengths of the struts of first, second, third, and fourth sets 3022, 3024, 3026, and 3028, which helps reduce the risk of infolding.

In some embodiments, the struts of first set 3022 can be tapered such that the width of the struts increases in the distal direction. For example, as shown in FIG. 4, a width 4084 of a proximal portion of a strut of first set 3022 can be less than a width 4086 of an intermediate portion of the strut of first set 3022, and width 4086 can be less than a width 4088 of a distal portion of the strut of first set 3022. In some embodiments, widths 4084, 4086, and 4088 are in a range from about 0.1 mm to about 1.2 mm. In some embodiments, widths 4084, 4086, and 4088 can be less than about 0.1 mm or more than about 1.2 mm. In some embodiments in which the struts of first set 3022 are tapered, the forces generated by compressing frame 3000 can be better distributed along the length of the struts of first set 3022. This force distribution can allow for more even compression of frame 3000, which reduces the risk of infolding.

In some embodiments, a width 4090 of an intermediate portion of the struts of second set 3024 is greater than width 4086 of the intermediate portion of the struts of first set 3022. In some embodiments, a width 4092 of an intermediate portion of the struts of third set 3026 is greater than width 4086. In some embodiments, widths 4094 and 4096 of intermediate portions of the struts of fourth and fifth sets 3028 and 3030, respectively, are greater than width 4086. In some embodiments, widths 4086, 4090, 4092, 4094, and 4096 can range from about 0.05 mm to about 0.35 mm. In some embodiments, widths 4086, 4090, 4092, 4094, and 4096 can be less than about 0.05 mm or more than about 0.35 mm. In some embodiments in which widths of intermediate portions of the struts distal to the struts of first set of struts 3022 are greater than the width of the intermediate portion of the struts of first set 3022, the forces generated by compressing frame 3000 can be better distributed through the struts of first, second, third, and fourth sets 3022, 3024, 3026, and 3028. This force distribution can allow for more even compression of frame 3000, which reduces the risk of infolding.

In some embodiments, the struts of second set 3024 and struts of third set 3026 that are joined together at third plurality of nodes 3038 to form second row of expandable cells 3040 can form a saddle portion of an inflow section of frame 3000 as described above with reference to saddle portion 1014 illustrated in FIG. 1. In some embodiments, the struts of first set 3022 and the struts of second set 3024 that are joined together at second plurality of nodes 3034 to form an outwardly flared portion of an inflow section of frame 3000 as described above with reference to outwardly flared portion 1016 illustrated in FIG. 1. In such embodiments in which the first row forms the outwardly flared portion and the second row forms the saddle portion, the force generated by crimping or recapturing the valve prosthesis can be better distributed. This force distribution can allow for more even compression of the valve prosthesis. Also, in such embodiments, the saddle portion of the valve prosthesis frame can function as a pivot point as the valve prosthesis is retracted within the delivery system.

FIGS. 5A-5G illustrates a valve prosthesis 5019 being loaded within a delivery sheath 5098 of a delivery catheter system according to an embodiment. The delivery catheter system may also include a guide wire 5100. Valve prosthesis 5019 includes an inflow section 5008, an intermediate section 5010, and an outflow section 5012 as described above with reference to FIGS. 1 and 2. A second row of expandable cells of inflow section 5008 can form a saddle portion, and a first row of expandable cells of inflow section 5008 can form an outwardly flared portion. As valve prosthesis 5019 is retracted within sheath 5098, for example, during crimping or recapture, the distal end portion of sheath 5098 engages valve prosthesis 5019, causing valve prosthesis 5019 to compress. During this compression, saddle portion 5016 functions as a pivot point, which may reduce infolding.

Figure 6A:
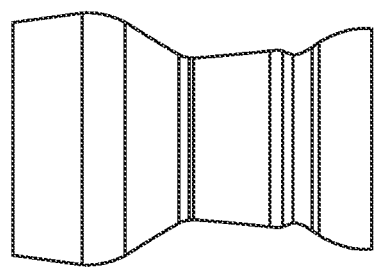
FIGS. 6A-6D schematically illustrate profiles of valve prostheses according to various embodiments.
Figure 6B:
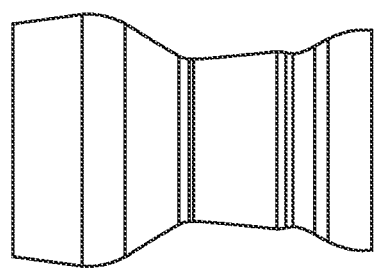
Figure 6C:
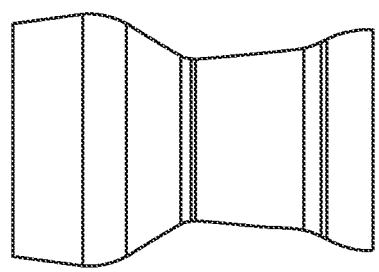
Figure 6D:
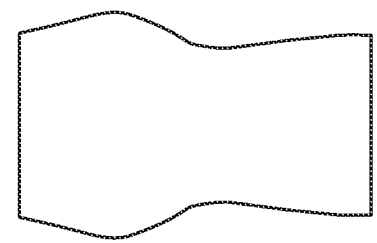

Notably, the invention is not limited valve prostheses having a profile as illustrated in FIGS. 1 and 2. For example, FIGS. 6A-6D schematically illustrate profiles of valve prostheses according to various embodiments. In FIG. 6A, the inflow section of the valve prosthesis does not include a saddle portion or an outwardly flared portion. In such embodiments, the inflow section may be substantially parallel with the intermediate section. In FIG. 6B, the inflow section of the valve prosthesis includes an outwardly flared portion, but does not include a saddle portion. In such embodiments, the intermediate section is adjacent the outwardly flared portion of the inflow section. In FIG. 6C, the inflow section of the valve prosthesis includes a saddle portion and an outwardly flared portion as described above with reference to FIGS. 1 and 2. FIG. 6D also illustrates a valve prosthesis having an inflow section that includes a saddle portion and an outwardly flared portion. But in this embodiment, the saddle portion is more deeply recessed relative to the surface of the intermediate section and the outwardly flared portion of the inflow section.

In some embodiments, a frame can have any combination of the above-described features or structures that are precisely adjusted and configured to reduce infolding.

Also, the frames disclosed above are not limited to valve prostheses frames and can be used with other devices. For example, the frames disclosed above can be used with an aneurysm graft such as an aortic aneurysm graft. The skilled artisan will appreciate that, in the context of such alternative applications, that the above identified strut and node dimensions would be adjusted for the intended application.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodi-

What is claimed is:

1. A prosthesis comprising:
a collapsible and re-expandable frame, the frame having an inflow edge and an outflow edge, wherein the frame includes at least first, second, third, and fourth sets of struts that form first, second, and third rows of expandable cells, each of the first set of struts, the second set of struts, the third set of struts, and the fourth set of struts having a distal end closer to the outflow edge and a proximal end closer to the inflow edge,
wherein struts of the first set of struts are connected to adjacent struts of the first set of struts at a first plurality of nodes at the inflow edge, the distal end of the first set of struts and the proximal end of the second set of struts are connected at a second plurality of nodes to define the first row of expandable cells, the distal end of the second set of struts and the proximal end of the third set of struts are connected at a third plurality of nodes to define the second row of expandable cells, and the distal end of the third set of struts and the proximal end of the fourth set of struts are connected at a fourth plurality of nodes to define the third row of expandable cells, and
wherein each node of the second plurality of nodes has a first length, each node of the third plurality of nodes has a second length, and each node of the fourth plurality of nodes has a third length, the first length being longer than the second length and the first length being longer than the third length, and
wherein a fourth length between centers of the first plurality of nodes and centers of the second plurality of nodes is longer than a fifth length between the centers of the second plurality of nodes and centers of the third plurality of nodes.

2. The prosthesis of claim 1, wherein each strut in the first and second sets of struts is connected to a node of the second plurality of nodes, each strut in the second and third sets of struts is connected to a node of the third plurality of nodes, and each strut in the third and fourth sets of struts is connected to a node of the fourth plurality of nodes.

3. The prosthesis of claim 1, wherein the first length is configured to distribute forces generated by compressing the frame towards the first set of struts.

4. The prosthesis of claim 1, wherein the first row of expandable cells forms an outwardly flared portion at the inflow edge of the frame and the second row of expandable cells forms a concave saddle portion that is adjacent and distal to the outwardly flared portion.

5. The prosthesis of claim 1, further comprising a valve body coupled to the frame.

6. The prosthesis of claim 1, wherein each node of the first plurality of nodes comprises a keyhole-shaped opening having a distal portion with a first width and a proximal portion with a second width that is greater than the first width, and wherein the distal portion of each keyhole-shaped opening opens to a corresponding expandable cell of the first row of expandable cells.

7. The prosthesis of claim 6, wherein the keyhole-shaped openings distribute forces generated by compressing the frame away from apices of the first plurality of nodes and provide a resulting force distribution at the inflow end of the prosthesis that permits the frame to be more evenly compressed while maintaining strength thereof.

8. The prosthesis of claim 1, wherein each strut of the first set of struts comprises a first proximal segment, a first intermediate segment with a first width, and a first distal segment, and wherein each strut of the second set of struts comprises a second proximal segment, a second intermediate segment with a second width, and a second distal segment, and wherein the second width of the second intermediate segment of each strut of the second set of struts is greater than the first width of the first intermediate segment of each strut of the first set of struts.

9. The prosthesis of claim 1, wherein each strut of the first set of struts comprises a first proximal segment with a first width, a first intermediate segment with a second width, and a first distal segment with a third width, the first width of the first proximal segment being smaller than the second width of the first intermediate segment and the second width of the first intermediate segment being smaller than the third width of the first distal segment.

10. A prosthesis comprising:
a collapsible and re-expandable frame, the frame having an inflow edge and an outflow edge, wherein the frame includes at least first, second, third, and fourth sets of struts that form first, second, and third rows of expandable cells, each of the first set of struts, the second set of struts, the third set of struts, and the fourth set of struts having a distal end closer to the outflow edge and a proximal end closer to the inflow edge,
wherein struts of the first set of struts are connected to adjacent struts of the first set of struts at a first plurality of nodes at the inflow edge, the distal end of the first set of struts and the proximal end of the second set of struts are connected at a second plurality of nodes to define the first row of expandable cells, the distal end of the second set of struts and the proximal end of the third set of struts are connected at a third plurality of nodes to define the second row of expandable cells, and the distal end of the third set of struts and the proximal end of the fourth set of struts are connected at a fourth plurality of nodes to define the third row of expandable cells,
wherein each strut in the first and second sets of struts is connected to a node of the second plurality of nodes, each strut in the second and third sets of struts is connected to a node of the third plurality of nodes, and each strut in the third and fourth sets of struts is connected to a node of the fourth plurality of nodes, and
wherein each node of the second plurality of nodes has a first length, each node of the third plurality of nodes has a second length, and each node of the fourth plurality of nodes has a third length, the first length being longer than the second length and the first length being longer than the third length, and
wherein a fourth length between centers of the first plurality of nodes and centers of the second plurality of nodes is longer than a fifth length between the centers of the second plurality of nodes and centers of the third plurality of nodes.

11. The prosthesis of claim 10, wherein the first length is configured to distribute forces generated by compressing the frame towards the first set of struts.

12. The prosthesis of claim 10, wherein the first row of expandable cells forms an outwardly flared portion at the inflow edge of the frame and the second row of expandable cells forms a concave saddle portion that is adjacent and distal to the outwardly flared portion.

13. The prosthesis of claim 10, further comprising a valve body coupled to the frame.

14. The prosthesis of claim 10, wherein each node of the first plurality of nodes comprises a keyhole-shaped opening having a distal portion with a first width and a proximal portion with a second width that is greater than the first width, and wherein the distal portion of each keyhole-shaped opening opens to a corresponding expandable cell of the first row of expandable cells.

15. The prosthesis of claim 14, wherein the keyhole-shaped openings distribute forces generated by compressing the frame away from apices of the first plurality of nodes and provide a resulting force distribution at the inflow end of the prosthesis that permits the frame to be more evenly compressed while maintaining strength thereof.

16. The prosthesis of claim 10, wherein each strut of the first set of struts comprises a first proximal segment, a first intermediate segment with a first width, and a first distal segment, and wherein each strut of the second set of struts comprises a second proximal segment, a second intermediate segment with a second width, and a second distal segment, and wherein the second width of the second intermediate segment of each strut of the second set of struts is greater than the first width of the first intermediate segment of each strut of the first set of struts.

17. The prosthesis of claim 10, wherein each strut of the first set of struts comprises a first proximal segment with a first width, a first intermediate segment with a second width, and a first distal segment with a third width, the first width of the first proximal segment being smaller than the second width of the first intermediate segment and the second width of the first intermediate segment being smaller than the third width of the first distal segment.

* * * * *